United States Patent
Sun et al.

(10) Patent No.: US 11,883,559 B2
(45) Date of Patent: Jan. 30, 2024

(54) BUILT-IN BIO-SLEEVE AND PREPARATION METHOD AND USE THEREOF

(71) Applicant: BEIJING JAYYALIFE BIOTECHNOLOGY CO., LTD., Beijing (CN)

(72) Inventors: Jihuang Sun, Beijing (CN); Hai Wang, Beijing (CN); Ang Zeng, Beijing (CN); Ming Bai, Beijing (CN); Hailin Zhang, Beijing (CN); Wei Wang, Beijing (CN); Xueyin Li, Beijing (CN); Wenjin Liu, Beijing (CN); Weiqiang Li, Beijing (CN); Qingdong Shi, Beijing (CN)

(73) Assignee: BEIJING JAYYALIFE BIOTECHNOLOGY CO, LTD., Beijing (CN)

( * ) Notice: Subject to any disclaimer, the term of this patent is extended or adjusted under 35 U.S.C. 154(b) by 713 days.

(21) Appl. No.: 15/733,094

(22) PCT Filed: May 17, 2018

(86) PCT No.: PCT/CN2018/087365
§ 371 (c)(1),
(2) Date: May 14, 2020

(87) PCT Pub. No.: WO2019/153568
PCT Pub. Date: Aug. 15, 2019

(65) Prior Publication Data
US 2020/0376164 A1    Dec. 3, 2020

(30) Foreign Application Priority Data
Feb. 8, 2018    (CN) .......................... 201810128163.6

(51) Int. Cl.
*A61K 35/36*    (2015.01)
*A61L 27/36*    (2006.01)
*A61L 27/50*    (2006.01)

(52) U.S. Cl.
CPC ......... *A61L 27/3687* (2013.01); *A61L 27/362* (2013.01); *A61L 27/3633* (2013.01); *A61L 27/3691* (2013.01); *A61L 27/50* (2013.01); *A61L 2430/32* (2013.01); *A61L 2430/34* (2013.01); *A61L 2430/40* (2013.01)

(58) Field of Classification Search
CPC .................................................... A61K 35/36
See application file for complete search history.

(56) References Cited

U.S. PATENT DOCUMENTS 5,632,778 A * 5/1997 Goldstein ........... A61L 27/3895
623/23.72

FOREIGN PATENT DOCUMENTS

| CN | 102218162 | 10/2011 |
| CN | 104888274 | 9/2015 |
| CN | 106693080 | 5/2017 |
| CN | 107233621 | 10/2017 |
| EP | 2873429 | 5/2015 |
| WO | WO 2017/114902 | 7/2017 |

OTHER PUBLICATIONS

Deng, Zhi-hong et al. "An experimental study on tissue engineered tympanic membrane in myringoplasty." China Academic Journal Electronic Publishing House, http://www.cnki.net. (Also Cited in ISR as: "Application of Acellular Dermal Tissue Engineering Tympanic Membrane in Tympanic Membrane Repair in Guinea Pigs." *Chinese Jounral of Otology*, vol. 6, No. 1, Dec. 31, 2008, pp. 115-118.
International Search Report for PCT/CN2018/087365.

* cited by examiner

*Primary Examiner* — Rosanne Kosson
(74) *Attorney, Agent, or Firm* — Barnes & Thornburg LLP

(57) ABSTRACT

The present invention relates to a built-in bio-sleeve and preparation method and use thereof. In order to provide a suitable built-in bio-sleeve material for dorsal nerve isolation surgery and penis enlargement surgery, a novel acellular allogeneic dermal matrix material is prepared in the present invention, which is manufactured into a built-in bio-sleeve for the treatment of premature ejaculation and short and small penis. The acellular allogeneic dermal matrix or the built-in bio-sleeve of the present invention is used for dorsal nerve isolation surgery, penis enlargement or lengthening surgery without cutting off the dorsal nerve, thereby avoiding the probability of psychological erectile dysfunction caused by the patient's worry about cutting off the dorsal nerve.

11 Claims, No Drawings

BUILT-IN BIO-SLEEVE AND PREPARATION METHOD AND USE THEREOF

CROSS REFERENCE TO RELATED APPLICATIONS

This application is a 371 national phase of PCT/CN2018/087365, filed May 17, 2018, the disclosure of which are incorporated, in their entirety, by this reference.

TECHNICAL FIELD

The present invention belongs to the technical field of tissue engineering of biomedical materials, and particularly relates to a built-in bio-sleeve and preparation method and use thereof.

BACKGROUND ART

Premature ejaculation (PE) is one of the most common clinical male diseases, with a morbidity accounting for 14% to 41% of adult males. It seriously affects the quality of sexual life, not only causes great harm to the body and mind of patients, but also threatens the marital relationship and family harmony. Previously, premature ejaculation was considered to be caused by mental and psychological factors, such as depression and high mental stress. However, recent studies have shown that some premature ejaculation has neuropathological organic lesions, that is, balanus hypersensitivity or hyperexcitability of sensory nerves in the balanus, resulting in low ejaculation threshold, such that the ejaculation latency is too short and thereby causing premature ejaculation.

Clinically, premature ejaculation is divided into primary premature ejaculation (which refers to men whose ejaculation latency is always less than 2 minutes since the first sexual life) and secondary premature ejaculation (which refers to men who had normal ejaculation latency in the past, and then whose ejaculation latency gradually becomes too short). At present, clinically, there is a lack of effective treatment for premature ejaculation, especially primary premature ejaculation, so urologists and male doctors have been troubled with premature ejaculation treatment for a long time. Professor Zhang Chunying from the Second Affiliated Hospital of Harbin Medical University conceives of the treatment of primary premature ejaculation by reducing the sensitivity of the balanus and thereby increasing the threshold of ejaculation to prolong the ejaculation latency and improving the quality of sexual life. Aiming to the cause, the Tullii RE penile neurotomy was first carried out in China, and it was expected that the primary premature ejaculation was treated by reducing the sensitivity of the balanus and increasing the threshold of ejaculation to prolong the time of sexual life, but the clinical effect is unstable. In order to conduct further researches, the regional anatomy of the penile dorsal nerve of 38 adult male corpses was studied. The results showed that the penile dorsal nerves averaged 3.55, which changed the academic viewpoint of 2 penile dorsal nerves that were previously thought to be accompanied with the penile dorsal artery. Thus, professor Zhang Chunying, et al designed the selective neurotomy of the penile dorsal nerve according to the new academic viewpoint.

The penile sensory pathway starts from the receptors in the penis skin, the balanus, the urethra and the corpus cavernosum. The exiting nerve fibers are fused to form penis dorsal nerve tract, and other nerve fibers are joined to form the internal pudendal nerves, which then rise to the spinal cord through the dorsal roots of the S2-4 nerves. After the receptors are activated, the pain, temperature and tactile information are transmitted to the hypothalamus and cortex for perception through the penile dorsal nerve, pudendal nerve, spinal cord, and spinothalamic tract. Sexual contact stimulates the penis skin and the balanus, and nerve impulses are transmitted through the penis dorsal nerves to initiate and maintain a reflex penile erection. It exists in primary premature ejaculation that the sensitivity of the balanus is excessively high, and the main factors determining the sensitivity of the balanus are the distribution of the penile nerves, the number of receptors and the threshold, as well as the nerve conduction pathway. After selective neurotomy of the distal end of the penile dorsal nerve, the sensitivity of the balanus can be reduced, the ejaculation stimulation threshold can be increased, the ejaculation latency can be prolonged, and the sexual life quality of the patient can be improved.

In recent years, it has been found that some patients who had undergone the penile dorsal nerve neurotomy have severe psychological disorders, they feel that their pleasure is decreased while the balanus is numb and the erection is difficult, resulting in psychological erectile dysfunction, which has caused pain to the patient and troubles to the doctor.

In the past, there were many ways to enlarge the penis, but mainly for short and small penis patients. It was not until the 1990s that the penile enlargement surgery was used in aesthetic surgery for normal penis. At present, the penile enlargement surgery is usually used for those who suffer short and small penis due to congenital or idiopathic penile dysplasia, or those who urge for the penile enlargement surgery to improve the quality of sexual life due to the poor quality of sexual life caused by the wife's vaginal relaxation after childbirth, or dissatisfaction with the diameter of his penis.

Injection of liquid silicone rubber, which was popular decades ago, is used to enlarge the penis. Because liquid silicone rubber is liable to cause complications such as rejection reaction, formation of nodules, abnormal morphology, and inguinal lymphadenectasis and the like, it has been banned. In the mid-1980s, the application of autologous fat injection to enlarge the penis came into use. However, because the preparations, injection methods and injection volumes of the fats are different, the effects were also different, resulting in relatively intense dispute. Due to possible absorption of fat, formation of fat nodules, dissatisfaction with shape, accumulation of distal fat and the like, multiple injections may be required, so some scholars do not agree with this method. In recent years, some scholars have used dermal fat flap free transplantation method and wrapping method with a whole dermal fat flap o perform the penis enlargement surgery. These methods have the advantages of no rejection reaction of autologous tissue, less damage to fat cells, rapid survival of dermis, natural appearance, and no foreign body sensation, and the effect is superior to fat injection. The disadvantage is that there is an incision scar in the donor area and there is a probability of calcification and necrosis. In addition, some scholars use the autologous saphenous vein to enlarge the penis, with the advantages of no rejection reaction, constant dissection, and simple operation. The disadvantage is that there is an incision scar in the donor area. In recent years, with the applications of synthetic materials, biomaterials and tissue engineering techniques, materials such as artificial blood vessels, expanded polytetrafluoroethylene (PTFE), silicone rubber prostheses and hyaluronidase gels are used in the penis enlargement surgery. However, these materials are generally expensive except silicone rubber prostheses, and some methods are relatively complicated to operate. Although these techniques are reported occasionally, no statistical data reports on the specific effects have been found.

The acellular built-in bio-sleeve, which is called the acellular allogeneic dermal matrix medical tissue built-in bio-sleeve, is taken from human allogeneic sheet or membranous tissue. The built-in bio-sleeve is biologically and chemically treated by decellularization technology to completely remove various cellular components that can be recognized by the host and those that can induce immune rejection reaction. If the skin used for transplantation contains cells, the immune response of the endothelial cells after transplantation may cause vasoconstriction, tissue ischemia, and tissue denaturation and necrosis. After decellularization treatment, human body tissue turns into a matrix and scaffold without cells, this material will generate immunologic inertia, so that immune rejection reaction will not occur, while the extracellular matrix components and the three-dimensional spatial framework thereof are completely retained.

Based on the above deficiencies, it is of practical significance to study an acellular allogeneic dermal matrix or built-in bio-sleeve that can be used for dorsal nerve block.

SUMMARY OF THE INVENTION

In order to adapt to the penile dorsal nerve isolation surgery and/or the penis enlargement surgery, a suitable built-in bio-sleeve material is provided. In the present invention, a new acellular allogeneic dermal matrix material is prepared by cooperative operation of multiple steps such as enzymatic treatment, surfactant ultrasonic treatment, DNA degradation treatment and the like, and it is made into a built-in bio-sleeve, which can be used for the treatment of premature ejaculation, short and small penis and the like.

The present invention provides an acellular allogeneic dermal matrix (built-in bio-sleeve) and preparation method thereof, as well as a method for dorsal nerve isolation surgery and a method for the penis enlargement surgery. The surgical method has the characteristics of small trauma, short operation time, safe and painless, less bleeding, quick recovery after surgery, strong anti-infection ability and good compatibility.

The invention provides the following technical solutions:

A preparation method of an acellular allogeneic dermal matrix, comprising the following steps:

Step 1), an allogeneic skin material is put into a solution of enzyme(s), soaked and subjected to shaking treatment to obtain a semi-finished product A, wherein the enzyme is phospholipase, or the enzymes are phospholipase and protease;

Step 2), the semi-finished product A is taken out, soaked with physiological saline, and subjected to shaking treatment to obtain a semi-finished product B;

Step 3), the semi-finished product B is put into a surfactant solution, and subjected to ultrasonic soaking treatment to obtain a semi-finished product C;

Step 4), the semi-finished product C is soaked with physiological saline, and subjected to shaking treatment to obtain a semi-finished product D;

Step 5), the semi-finished product D is put into a container containing a DNA hydrolase solution, and subjected to shaking treatment to obtain a semi-finished product E;

Step 6), the semi-finished product E is soaked with physiological saline, and subjected to shaking treatment to obtain a semi-finished product F;

Step 7), the semi-finished product F is washed and soaked with water for injection to obtain a finished product G, i.e., the acellular allogeneic dermal matrix, which can be directly used as a material for the penile dorsal nerve surgery or used for preparing a material for the penile dorsal nerve surgery.

Generally, the acellular allogeneic dermal matrix prepared by the above method can be stored in physiological saline. In order to extend the storage life, sterilization treatment (for example, irradiation sterilization) can also be performed.

In order to facilitate the storage and transportation of the above-mentioned acellular allogeneic dermal matrix and prolong its effective period, the above method further comprises the following steps:

Step 8): the finished product G is taken out, packaged, and sterilized to obtain a finished product H; or the finished product G is taken out, placed in a solution containing a lyoprotectant for freeze-drying, packaged, and sterilized to obtain a finished product H.

Further, the protease in the step 1) includes one or more of trypsin, bromelain, papain, dispase (neutral protease) and the like.

In some embodiments, the enzyme in the step 1) is phospholipase, or one or more of phospholipase, trypsin, bromelain, papain, and dispase. Further, the solution of enzyme(s) has a pH of 7.0 to 8.0. Preferably, the concentration of the phospholipase is 0.1 g/L to 0.4 g/L, and/or the concentration of the protease (or any one of trypsin, bromelain, papain, and dispase) is 0.1 g/L to 0.3 g/L. Further, the phospholipase is one or more of phospholipase A1, phospholipase A2, phospholipase C, and phospholipase D. Preferably, the mass ratio of phospholipase A1, phospholipase A2, phospholipase C and phospholipase D is 1:1:1:1.

In some embodiments, the conditions for shaking treatment in the step 1) are as follows: shaking for 0.5 h to 4 h at a shaking speed of 10 rpm to 200 rpm and a temperature of 10° C. to 40° C.

In some embodiments, the surfactant solution in the step 3) contains 0.1 to 0.3 g/L of SDS (sodium dodecyl sulfate), or the surfactant solution contains 0.1 to 0.3 g/L of Triton X-100 (polyethylene glycol octyl phenyl ether). Further, the conditions for ultrasonic soaking are as follows: ultrasonic treatment for 3 to 8 minutes under 40 to 80 KHz and 100 to 400 W, soaking for 2 to 4 hours, and repeating the above operation for 2 to 4 times, at a temperature of 1 to 20° C.

In some embodiments, the DNA hydrolase solution in the step 5) has a concentration of 4 to 8 g/L and a pH is 7.0 to 8.0, and the preferred concentration is 4 to 6 g/L.

In some embodiments, the conditions for shaking treatment in the step 5) are as follows: shaking for 2 to 8 h at a shaking speed of 10 to 200 rpm and a temperature of 10 to 40° C.

In some embodiments, the conditions for shaking treatment in the step 2), step 4), and step 6) are as follows: shaking is conducted for 1 to 2 h at a shaking speed of 80 to 150 rpm, then the physiological saline is replaced to continue the shaking treatment, and the above operation is repeated for 4 to 6 times, at a temperature of 1 to 5° C.

In some embodiments, the conditions for washing and soaking with water for injection in the step 7) are as follows: shaking is conducted for 2 h at a shaking speed of 80 to 150 rpm and a temperature of 1 to 5° C., then the water for injection is replaced to continue the shaking treatment, and the above operation is repeated for 4 to 6 times.

In some embodiments, the lyoprotectant solution in the step 8) comprises a phosphate buffer solution, hyaluronic acid, and sugar, wherein the concentration of the hyaluronic acid is 0.4 to 0.8 mg/100 mL, the concentration of the sugar is 10 to 20 mg/100 mL, and the sugar is one or more of trehalose, lactose, sucrose, glycerin, mannitol, sorbitol, mannose, and glucose. The phosphate buffer solution (PBS) can be prepared according to the conventional method in the art, preferably it is 10 mmol/L phosphate buffer solution at pH 7.0.

Specifically, the freeze-drying step is as follows: placing the finished product G in an oven at 5° C., holding at 5° C. in the oven for 1 h, cooling to −40° C. and holding for 1 h, heating to −18° C. and holding for 1 h, cooling again to −35° C. and holding for 1 h, starting a vacuum pump to evacuate the drying oven to a vacuum degree of 5 to 10 Pa; heating a partition board to −30° C. in 2 h, evacuating the drying oven to a vacuum degree of 1 to 5 Pa and holding for 15 h; heating the partition board to 0° C. in 1 h and holding for 10 h, then measuring the pressure rise until the pressure rise is less than 1 Pa; heating the partition board to 10° C. in 1 h and holding for 10 h, and measuring the pressure rise until the pressure rise is less than 1 Pa; heating the partition board to 25° C. in 0.5 h and holding for 8 h, and measuring the pressure rise until the pressure rise is less than 1 Pa. The vacuum degree in said oven should not be higher than 30 Pa throughout the drying process.

In some embodiments, the packaging in the step 8) is performed by putting the semi-finished product G into a packaging bag and sealing, the sterilization is performed by cobalt-60 irradiation, and the irradiation dose is 20 to 30 kGy.

Based on the common knowledge in the art, the above various preferred conditions can be combined with one another to obtain the preferred examples of the present invention.

The allogeneic skin material of the present invention is derived from the skin of a voluntary donor (e.g., non-living donor).

The present invention also includes an acellular allogeneic dermal matrix prepared by the above method, or a further prepared material for penile dorsal nerve surgery, material for penis enlargement surgery, and penis built-in bio-sleeve.

The acellular allogeneic dermal matrix prepared by the present invention has a suture strength of up to 16 N to 18 N.

The acellular allogeneic dermal matrix prepared by the present invention (material for penile dorsal nerve surgery, material for penis enlargement surgery, and penis built-in bio-sleeve) is preferably subjected to the following operations before use: completely soaking (rehydration) it in physiological saline at 20° C. to 35° C. for 15 minutes.

The above-mentioned acellular allogeneic dermal matrix (material for penile dorsal nerve surgery, material for penis enlargement surgery, and penis built-in bio-sleeve) can be made into an appropriate size according to actual requirements.

The acellular allogeneic dermal matrix of the present invention (material for penile dorsal nerve surgery, material for penis enlargement surgery, and penis built-in bio-sleeve) is stored in a cool and dry place under a relative humidity of less than or equal to 45%.

The present invention also comprises the use of the above-mentioned acellular allogeneic dermal matrix in the preparation of a penile dorsal nerve surgical material or a penis enlargement surgical material or a penis built-in bio-sleeve.

The present invention also comprises the use of the above-mentioned acellular allogeneic dermal matrix (material for penile dorsal nerve surgery, material for penis enlargement surgery, and penis built-in bio-sleeve) in a penile dorsal nerve isolation surgery and/or a penis enlargement surgery.

Another aspect of the present invention is to provide a surgical kit, comprising the aforementioned acellular allogeneic dermal matrix (material for penile dorsal nerve surgery, material for penis enlargement surgery, and penis built-in bio-sleeve). The kit may further comprise scalpels, surgical scissors, hemostatic forceps, tweezers, suture needles, 5-0 absorbable surgical sutures, ampoules containing water for injection, and syringes.

The present invention improves and optimizes the preparation process of the acellular allogeneic dermal matrix according to the needs of the penile dorsal nerve isolation surgery and penis enlargement surgery. The product is obtained by subjecting the skin from the human body of a donor to special biotechnical treatments to remove all cells in the tissue that can induce a host immune rejection reaction while the extracellular matrix with the same structure as the original tissue is completely retained. Freeze-drying treatment is performed according to needs to make the product convenient for storage and transportation. Through continuous research on the product, it is found that because the stereoscopic scaffold structure of the original tissue is completely retained while the components inducing immune rejection reaction are removed, as a cell scaffold, the product has the effect of inducing tissue formation. It can be recognized as autologous tissue by human tissue cells after being implanted into the human body, and soon new blood vessels and fibroblasts grow therein, guiding cells to grow in order along its collagen framework, so as to achieve the purpose of supplementation, especially rapid repair. It has good histocompatibility and mechanical properties, and can exist for a long time and become a part of human tissue, thus completing the repair of tissue defects and reconstruction.

The present invention also provides a method for penile dorsal nerve isolation surgery, which adopts the above-mentioned acellular allogeneic dermal matrix (material for penile dorsal nerve surgery, material for penis enlargement surgery, and penis built-in bio-sleeve). The surgical method includes: after penile root nerve blocking anesthesia, prepuce circular resection is performed for those with redundant prepuce, and for those who had undergone prepuce circular resection, the skin of 3 to 5 cm in length is opened up along the original incision on the dorsal side of the penis; the superficial fascia and deep fascia are sequentially opened up until the albuginea is fully exposed, dissociating is performed carefully until reaching the coronary sulcus, and an acellular allogeneic dermal matrix is manufactured into a built-in bio-sleeve according to the need and sutured to be fixed on the albuginea, with the distal end of the bio-sleeve reaching the coronary sulcus and two sides of the bio-sleeve not wrapping around the urethra; the fascias and skin are sutured layer by layer; and the penis is appropriately subjected to pressure bandaging. Meanwhile, after being implanted into the human body, the acellular allogeneic dermal matrix or the built-in bio-sleeve needs to have a high affinity with the normal tissue of the human body, which requires a certain degree of softness.

Post-surgery treatment:
1. The penis is appropriately subject to pressure bandaging for 1 to 3 weeks after surgery.
2. Pay attention to the situation of preputial edema and the penile blood supply after surgery.
3. Penile erection is inhibited by oral administration of 12.5 mg of chlorpromazine (one time per day) and 25 mg of promethazine (one time per day) two days in advance.
4. The suture is taken out 8 to 10 days after surgery (as to absorbable suture, the suture may not be taken out).
5. Sexual life is prohibited for 6 weeks after surgery.

Key points in surgery:
1. An appropriate material is selected according to the specific situations of the patient before surgery.
2. Try to do a complete dissociation by one step in surgery, and it must be prohibited to repeat operation at the same position so as to avoid post-surgery refractory edema. The distal end of the bio-sleeve of the dissociation must reach the coronal sulcus, and the urethra cannot be involved on both sides of the bio-sleeve.
3. At least 1 cm of the inner plate of the prepuce was retained, so as to avoid large tension after surgery and poor incision healing. However, 1.5 cm cannot be exceeded, otherwise the inner plate edema will occur and not disappear for a long time after surgery.
4. Post-surgery bandaging is necessary, but must be appropriate. Except in special circumstances, the gauze cannot be opened within 3 days after surgery.

The method for penile dorsal nerve isolation surgery of the present invention mainly utilizes an acellular allogeneic dermal matrix (material for penile dorsal nerve surgery, material for penis enlargement surgery, and penis built-in bio-sleeve) to cover the penile dorsal nerve, thereby reducing the sensitivity of the penile coronary sulcus and the prepuce skin in sexual life, so as to prolong the ejaculation latency and improve the quality of sexual life. Moreover, the present surgical method does not cut off the dorsal nerve, thereby avoiding the probability of psychological erectile dysfunction caused by the patient's worry about cutting off the dorsal nerve.

The present invention also provides a method for penis enlargement surgery, which adopts the above-mentioned acellular allogeneic dermal matrix (material for penile dorsal nerve surgery, material for penis enlargement surgery, and penis built-in bio-sleeve). The surgical method comprises: a prepuce circular incision is made at a distance of about 1 cm away from the coronary sulcus, the superficial fascia and deep fascia are sequentially opened up to reach the surface of the albuginea, dissociating is performed downward along the surface of the albuginea to the root of the penis, and the prepuce of the penis is degloved. An acellular allogeneic dermal matrix is manufactured into a built-in bio-sleeve according to the need and sutured to be fixed on the albuginea of the penis, with the distal end of the bio-sleeve beneath the coronary sulcus and two sides of the bio-sleeve reaching the sulcus between the corpus cavernosum and the cavernous body of urethra. The incisions are sutured layer by layer, and the penis is appropriately subjected to pressure bandaging. There is a need to increase the suture density, so the built-in bio-sleeve of the acellular allogeneic dermal matrix is required to have a relatively high suture strength. Meanwhile, after being implanted into the human body, the acellular allogeneic dermal matrix or the built-in bio-sleeve needs to have a high affinity with the normal tissue of the human body, which requires a certain degree of softness.

For post-surgery treatment, refer to the above-mentioned penile dorsal nerve isolation surgery.

The above-mentioned penile dorsal nerve isolation surgery and penis enlargement surgery also include a post-surgery recovery period. Physiological saline and ceftazidime may be intravenously infused or glucose saline and clindamycin may be intravenously infused once a day according to the situation in the post-surgery recovery period. As a further preferred embodiment, 250 ml of 0.9% physiological saline and 3 g of ceftazidime, or 250 ml of 5% glucose saline and 0.6 g of clindamycin are intravenously infused each time.

As a further preferred embodiment of the present invention, the post-surgery recovery period is 10 to 15 days, physiological saline and ceftazidime or glucose saline and clindamycin are intravenously infused for the first five days, and the drug is changed on the sixth day. Glucose saline and clindamycin or physiological saline and ceftazidime are intravenously infused from the sixth day to the fifteenth day according to the recovery condition of the wound.

As the quality requirements of the people's spiritual life and sexual life continue to increase, the market demand for genital plastic surgery continues to grow. Because the male genital surgery site is private and wet, the surgery seems simple, but involves many fields such as minimally invasive surgery, cell biology, immunology, and materials science. At present, the medical institutions in China have various methods for the penis enlargement surgery, but each method has its own risks and benefits. Moreover, the good and bad are intermingled, and unsuccessful phenomena often occur.

The method for penis enlargement surgery provided by the present invention does not involve testicles and cavernous body, does not affect normal physiological functions, and can simultaneously release the suspensory ligament during the operation to lengthen the penis, and reduce the sensitivity of the dorsal nerve to effectively extend the time of sexual life. Meanwhile, after being implanted into the human body, the above-mentioned acellular allogeneic dermal matrix material (material for penile dorsal nerve surgery, material for penis enlargement surgery, and penis built-in bio-sleeve) has a high affinity with the normal tissue of the human body, and is a living viable tissue. The normal cells of the human body grow and proliferate on the three-dimensional scaffold of the above-mentioned material. The cell processing technology is used to manufacture the material for enlargement, no rejection phenomenon occurs, and a new extracellular matrix component is secreted to form a body's own tissue. Therefore, there is no foreign body sensation after surgery, no surgery traces can be seen, the appearance is natural, the hand feel is real, and the enlargement effect is obvious. Compared with the conventional method, the present invention has the advantages of simple operation, small surgical trauma, short operation time, safe and painless, quick recovery after surgery, and strong anti-infection ability, and can effectively solve the problem of unsatisfactory sexual life caused by the primary premature ejaculation problem of the male, so as to greatly improve the quality of sexual life.

The dorsal nerve isolation surgery can also achieve a penis enlargement effect. In addition, in the present invention, it is also found that the penile dorsal nerve isolation surgery and the penis enlargement surgery can be performed simultaneously, without causing local necrosis of the penile epidermis, and the success rate of the surgery is high.

The acellular allogeneic dermal matrix (material for penile dorsal nerve surgery, material for penis enlargement surgery, and penis built-in bio-sleeve) of the present invention can meet the needs of the dorsal nerve isolation, penis enlargement, and penis lengthening surgery. In the present invention, decellularization is performed by enzyme treatment in combination with ultrasonic treatment with a surfactant solution, which can achieve good decellularization effect with less damage to the dermal matrix, is beneficial to improve mechanical properties of the tissue product to obtain better elasticity and toughness, and can improve the tearing strength and suture strength of the tissue and contribute to remove the residual DNA in the dermal matrix during the DNA hydrolase treatment step, thereby reducing cytotoxicity and rejection reaction.

In summary, the acellular allogeneic dermal matrix (material for penile dorsal nerve surgery, material for penis enlargement surgery, and penis built-in bio-sleeve) of the present invention has the following advantages: (1) in terms of product properties, the acellular allogeneic dermal matrix or the built-in bio-sleeve of the present invention is a product from an improved process, the mechanical properties of the product are suitable for surgery and the suture strength thereof is 16 N to 18 N; (2) in terms of effects of the product, the acellular allogeneic dermal matrix or the built-in bio-sleeve of the present invention has no immune rejection reaction, can rapidly induce tissue regeneration, and has a soft texture after implantation, no sense of contour, good in-vivo compatibility, and stable scaffold or template function; (3) the acellular allogeneic dermal matrix or built-in bio-sleeve is used for penis enlargement or lengthening or dorsal nerve isolation surgery in a manner without cutting off the dorsal nerve, thereby avoiding the probability of psychological erectile dysfunction caused by the patient's worry about cutting off the dorsal nerve.

SPECIFIC MODES FOR CARRYING OUT THE EMBODIMENTS

The following Examples are intended to illustrate the present invention, but are not intended to limit the scope of the present invention. The Examples for which specific techniques or conditions are not indicated, are performed according to the techniques or conditions described in literatures in the art, or in accordance with the product specifications. The reagents or instruments used without indicating the manufacturers are all conventional products that can be purchased through regular channels.

Example 1

Preparation Method of an Acellular Allogeneic Dermal Matrix

An allogeneic dermis raw material was put into an enzyme solution comprising phospholipase at a concentration of 0.3 g/L and trypsin at a concentration of 0.1 g/L and having a pH of 7.0, at a temperature of 37° C., and subjected to shaking at 100 rpm for 2 h, the enzyme solution was replaced once, and the above process was repeated once to obtain a semi-finished product A. The phospholipase is a mixture of phospholipase A1, phospholipase A2, phospholipase C and phospholipase D at a mass ratio of 1:1:1:1.

The semi-finished product A was taken out, put into a container containing a physiological saline solution and soaked in physiological saline and subjected to shaking for 2 h at a shaking speed of 80 rpm and a temperature of 2° C. for 3 times to obtain a semi-finished product B.

The semi-finished product B was put into a solution containing 0.2 g/L Triton X-100, and subjected to ultrasonic treatment under 50 KHz and 220 W for 5 min and soaking for 3 h. The process was repeated for 3 times to obtain a semi-finished product C.

The semi-finished product C was taken out, put into a container containing a physiological saline solution and soaked in physiological saline. Shaking was performed for 2 h at a temperature of 2° C. and a shaking speed of 80 rpm for 3 times to obtain a semi-finished product D.

The semi-finished product D was put into a container containing a DNA hydrolase solution with a concentration of 5 g/L and a pH of 7.0. Shaking treatment was performed at a temperature of 37° C. and a shaking speed of 20 rpm for 4 h to obtain a semi-finished product E.

The semi-finished product E was put into a container containing a physiological saline solution and soaked in physiological saline. Shaking was performed at a temperature of 2° C. and a shaking speed of 80 rpm for 2 h for 3 times to obtain a semi-finished product F.

The semi-finished product F was put into a container containing water for injection and soaked in physiological saline. Shaking was performed at a temperature of 2° C. and a shaking speed of 80 rpm for 2 h for 3 times to obtain a finished product G.

The finished product G was taken out, put into a packaging bag, flattened, sealed, subjected to cobalt-60 irradiation at an irradiation dose of 20 to 30 kGy, and taken out to obtain a finished product H. The suture strength was 17.7 N.

Example 2

Preparation Method of an Acellular Allogeneic Dermal Matrix

An allogeneic dermis raw material was put into an enzyme solution comprising phospholipase at a concentration of 0.2 g/L and trypsin at a concentration of 0.2 g/L and having a pH of 7.0 at a temperature of 37° C., and subjected to shaking at 100 rpm for 2 h, the enzyme solution was replaced once, and the above process was repeated once to obtain a semi-finished product A. The phospholipase is a mixture of phospholipase A1, phospholipase A2, phospholipase C and phospholipase D at a mass ratio of 1:1:1:1.

The semi-finished product A was taken out, put into a container containing a physiological saline solution and soaked in physiological saline. Shaking was performed for 2 h at a shaking speed of 80 rpm and a temperature of 2° C. for 3 times to obtain a semi-finished product B.

The semi-finished product B was put into a solution containing 0.2 g/L SDS and 10 mM EDTA, and subjected to ultrasonic treatment under 50 KHz and 220 W for 7 min and soaking for 2 h. The above process was repeated for 3 times to obtain a semi-finished product C.

The semi-finished product C was taken out, put into a container containing a physiological saline solution and soaked in physiological saline. Shaking was performed for 1 h at a shaking speed of 100 rpm and a temperature of 4° C. for 3 times to obtain a semi-finished product D.

The semi-finished product D was put into a container containing a DNA hydrolase solution with a concentration of 7 g/L and a pH of 7.0. Shaking treatment was performed at a temperature of 30° C. and a shaking speed of 30 rpm for 3 h to obtain a semi-finished product E.

The semi-finished product E was put into a container containing a physiological saline solution and soaked in physiological saline. Shaking was performed at a shaking speed of 100 rpm and a temperature of 4° C. for 1 h for 3 times to obtain a semi-finished product F.

The semi-finished product F was put into in a container containing water for injection and soaked in physiological saline. Shaking was performed at a temperature of 2° C. and a shaking speed of 80 rpm for 2 h for 3 times to obtain a finished product G.

The finished product G was taken out and put into a lyoprotectant solution, placed in an oven at 5° C., followed by holding for 1 h, cooling to −40° C. and holding for 1 h, heating to −18° C. and holding for 1 h, cooling again to −35° C. and holding for 1 h, starting a vacuum pump to evacuate the drying oven to a vacuum degree of 5 to 10 Pa; heating a partition board to −30° C. in 2 h, evacuating the drying oven to a vacuum degree of 1 to 5 Pa and holding for 15 h; heating the partition board to 0° C. in 1 h and holding for 10 h, then measuring the pressure rise until the pressure rise was less than 1 Pa; heating the partition board to 10° C. in 1 h and holding for 10 h, and measuring the pressure rise until the pressure rise was less than 1 Pa; heating the partition board to 25° C. in 0.5 h and holding for 8 h, and measuring the pressure rise until the pressure rise was less than 1 Pa. The vacuum degree in said oven should not be higher than 30 Pa throughout the drying process. A semi-finished product G1 was obtained.

The lyoprotectant solution was composed of phosphate buffer solution (10 mmol/L, pH 7.0), hyaluronic acid and trehalose, wherein the concentration of hyaluronic acid was 0.6 mg/100 mL, and the concentration of trehalose was 10 mg/100 mL.

The semi-finished product G1 was taken out, put into a packaging bag, flattened, sealed, subjected to cobalt-60 irradiation at an irradiation dose of 20 to 30 kGy, and taken out to obtain a finished product H. The suture strength was 16.8 N.

Experimental Example 1

Acellular Allogeneic Dermal Matrix (Built-In Bio-Sleeve) for Dorsal Nerve Isolation Surgery Surgical method: After penile root nerve blocking anesthesia, prepuce circular resection was performed for those with redundant prepuce, and for those who had undergone prepuce circular resection, the skin of 3 to 5 cm in length was opened up along the original incision on the dorsal side of the penis. The superficial fascia and deep fascia were sequentially opened up until the albuginea was fully exposed. Dissociating was performed carefully until reaching the coronary sulcus, and an acellular allogeneic dermal matrix was manufactured into a built-in bio-sleeve according to the need and sutured to be fixed on the albuginea, with the distal end of the bio-sleeve reaching the coronary sulcus and two sides of the bio-sleeve not wrapping around the urethra. The fascias and skin were sutured layer by layer, and the penis was appropriately subjected to pressure bandaging.

Post-Surgery Treatment:
1. The penis was appropriately subjected to pressure bandaging for 1 to 3 weeks after surgery.
2. Pay attention to the situation of preputial edema condition and the penile blood supply after surgery.
3. Penile erection was inhibited by oral administration of 12.5 mg of chlorpromazine (one time per day) and 25 mg of promethazine (one time per day) two days in advance.
4. The suture was taken out 8 to 10 days after surgery (as to absorbable sutures, the suture may not be taken out).

Typical Case 1

A person surnamed Li, who was male, 37 years old, and suffers from too fast ejaculation. The penile dorsal nerve isolation surgery was performed as follows: a 5 cm transverse incision was made on the dorsal side of the penis, and the superficial fascia and deep fascia of the penis were sequentially opened up until the penis albuginea was fully exposed. The acellular allogeneic dermal matrix of Example 1 was prepared into a built-in bio-sleeve (2 cm*3 cm) which was sutured to be fixed on the penis albuginea, with the distal end of the bio-sleeve very close to the coronary sulcus, and a 5-0 absorbable suture was used to suture layer by layer.

After surgery, the penis was bandaged with an elastic bandage, the drug was changed daily and the wound condition and blood supply of the skin was observed.

The ejaculation latency before surgery was 1 min, and at a return visit after 6 weeks, the ejaculation latency was 8 min.

At a return visit 3 months after surgery, the ejaculation latency was 5 min to 10 min.

Typical Case 2

A person surnamed Li, who was male, 27 years old, and suffers from too fast ejaculation. The penile dorsal nerve isolation surgery was performed as follows: a 5 cm transverse incision was made on the dorsal side of the penis, and the superficial fascia and deep fascia of the penis were sequentially opened up until the penis albuginea was fully exposed. The acellular allogeneic dermal matrix of Example 2 was prepared into a built-in bio-sleeve (2 cm*3 cm) which was sutured to be fixed on the penis albuginea, with the distal end of the bio-sleeve very close to the coronary sulcus, and a 5-0 absorbable suture was used to suture layer by layer.

After surgery, the penis was bandaged with an elastic bandage, the drug was changed daily and the wound condition and blood supply of the skin was observed.

The ejaculation latency before surgery was 2 min, and at a return visit after 6 weeks, the ejaculation latency was 9 min.

At a return visit 3 months after surgery, the ejaculation latency was 5 min to 10 min.

Comparative Example 1

Penile Dorsal Nerve Block Surgery

Mr. Wang, who was male, 38 years old and suffers from primary premature ejaculation.

Penile dorsal nerve block surgical treatment was performed as follows: a transverse incision was made at the penile dorsal coronal sulcus under local anesthesia. The Buck fascia was separated from the albuginea to expose the branches of the penile dorsal nerve. It was found that the branches of the nerve were up to 7. The main trunk of the penile dorsal nerve and three branches thereof were retained, the remaining four branches of the nerve dissociated for 2 to 3 CM was cut off, and the incision was sutured.

The incision was healed well after surgery, and Mr. Wang began sexual life three weeks after surgery. The erection was good, and the ejaculation time was prolonged and could reach about 6 min after two months.

Comparative Example 2

Penis Catgut Embedding Surgery for Desensitization

A person surnamed Zhou, who was male, 32 years old, and suffers from too fast ejaculation. The penis catgut embedding surgery for desensitization was performed as follows: routine disinfection was performed, the prepuce was pushed backwards to fully expose the inner plate of the prepuce, the frenum was unfolded, but the frenum cannot be stretched too tight so as to prevent the catgut from being too close to the urethral orifice. A 2-0 catgut was threaded through a small round needle. The needle was inserted at a distance of about 1 to 1.5 cm away from the root of the frenum, and subcutaneously moved underneath the frenum for a length of about 1 cm. The needle was withdrawn at a distance of about 0.2 cm away from the root of the frenum. The catgut was cut off at two ends for inserting and withdrawing the needle, and the frenum was fully tightened again to allow the catgut to be embedded in the frenum.

Five days after surgery, the patient was advised to squeeze the catgut at the frenum for 3 to 5 min every day until 4 weeks later when sexual life can be regular. The sutures of the inner plate and the outer plate were removed 7 days after surgery.

The ejaculation latency before surgery was 1 min, and at a return visit after 6 weeks, the ejaculation latency was 6 min.

At a return visit 3 months after surgery, the ejaculation latency was 5 min to 9 min.

From the results of Experimental Example 1 and Comparative Examples 1 to 2, it can be seen that the built-in bio-sleeve of the acellular allogeneic dermal matrix prepared by the method of the present invention was used for the dorsal nerve isolation surgery, the ejaculation latency before surgery was 1 min, and at a return visit 3 months after surgery, the ejaculation latency was 5 min to 10 min. The built-in bio-sleeve medical tissue of the acellular allogeneic dermal matrix was mainly used to cover the penis dorsal nerve, thereby reducing the sensitivity of the penis coronal sulcus and prepuce skin during sexual life to prolong the ejaculation latency and improve the quality of sexual life. Moreover, the built-in bio-sleeve of the acellular allogeneic dermis matrix was used for penis enlargement and lengthening, and the dorsal nerve was not cut off in the dorsal nerve isolation surgery, thereby avoiding the probability of psychological erectile dysfunction caused by the patient's worry about cutting off the dorsal nerve. For the penile dorsal nerve block surgery, the ejaculation latency before surgery was 1 min, and at a return visit 3 months after surgery, the ejaculation latency was 5 min to 9 min. The penile dorsal nerve block surgery can treat primary premature ejaculation by reducing the sensitivity of the balanus and improving the ejaculation threshold to prolong the time of sexual life, but the clinical effect is unstable. In recent years, it has been found that some patients who had undergone penile dorsal nerve block surgery have severe psychological disorders. They feel that their pleasure is decreased while the balanus is numb and the erection is difficult, resulting in psychological erectile dysfunction, which has caused pain to the patient and troubles to the doctor. For the penis catgut embedding surgery for desensitization, the ejaculation latency before surgery was 1 min, and at a return visit 3 months after surgery, and the ejaculation latency was 5 min to 9 min. The penis catgut embedding surgery for desensitization was based on the rules of selecting acupoints of the catgut embedding therapy, a catgut was implanted at the penis frenum, and the catgut embedded in the acupoint or nerve sensitive area was used to replace the acupuncture needle to exert a lasting weak and mild benign excitatory stimulation effect on the local acupoints, so as to strengthen the inhibition on the brain ejaculation center to make the penis nerve not be so "sensitive", and the brain's control on ejaculation behavior is strengthened, so as to solve the problem of premature ejaculation.

Experimental Example 2

Acellular Allogeneic Dermal Matrix (Built-In Bio-Sleeve) for Penis Enlargement Surgery Surgical method: a prepuce circular incision was made at a distance of about 1 cm away from the coronary sulcus, the superficial fascia and deep fascia were sequentially opened up to reach the surface of the albuginea, dissociating was performed downward along the surface of the albuginea to the root of the penis, and the prepuce of the penis was degloved. An acellular allogeneic dermal matrix was manufactured into a built-in bio-sleeve according to the need and sutured to be fixed on the albuginea of the penis, with the distal end of the bio-sleeve beneath the coronary sulcus and two sides of the bio-sleeve reaching the sulcus between the corpus cavernosum and the cavernous body of urethra. The incisions were sutured layer by layer, and the penis was appropriately subjected to pressure bandaging.

Post-Surgery Treatment:
1. The penis was appropriately subjected to pressure bandaging for 1 to 3 weeks after surgery.
2. Pay attention to the situation of preputial edema and the penile blood supply after surgery.
3. Penile erection was inhibited by oral administration of 12.5 mg of chlorpromazine (one time per day) and 25 mg of promethazine (one time per day) two days in advance.
4. The suture was taken out 8 to 10 days after surgery (as to absorbable suture, the suture may not be taken out).
5. Sexual life was prohibited for 6 weeks after surgery.

Typical Case 1

A person surnamed Xiong, who was male, 38 years old, and felt his penis was relatively thin. The penis lengthening enlargement surgery was performed as follows: a prepuce circular incision was made at a distance of about 1 cm away from the coronary sulcus of the balanus, the superficial fascia and deep fascia were sequentially opened up to reach the surface layer of the albuginea, dissociating was performed downward to the root of the penis, and the prepuce of the penis was degloved. The acellular allogeneic dermal matrix of Example 2 was manufactured into a built-in bio-sleeve according to the need and sutured to be fixed on the surface of the penis albuginea layer, with two sides of the bio-sleeve reaching the sulcus between the corpus cavernosum and the cavernous body of urethra. The incisions were sutured layer by layer with a 5-0 absorbable suture, and the penis was appropriately subjected to pressure bandaging.

After surgery, the penis was bandaged with an elastic bandage, the drug was changed daily and the wound condition and blood supply of the skin was observed.

The penis had a circumferential diameter of 7.5 cm in natural state before surgery, and a circumferential diameter of 12 cm in natural state after surgery.

The wound was healed 12 days after surgery, and the sexual function was measured to be normal. A following visit for as long as 46 months was made after surgery. The penile erection was natural and powerful with a nice appearance. The penis was obviously enlarged than that before surgery. The degree of satisfaction with sexual life was high. The male had more confidence without other complications.

Typical Case 2

A person surnamed Luo, who was male, 36 years old, and felt his penis was short. The penis lengthening enlargement surgery was performed as follows: a prepuce circular incision was made at a distance of about 1 cm away from the coronary sulcus of the balanus, the superficial fascia and deep fascia were sequentially opened up to reach the surface layer of the albuginea, dissociating was performed downward to the root of the penis, and the prepuce of the penis was degloved. The acellular allogeneic dermal matrix of Example 1 was manufactured into a built-in bio-sleeve according to the need and sutured to be fixed on the surface of the penis albuginea layer, with two sides of the bio-sleeve reaching the sulcus between the corpus cavernosum and the cavernous body of urethra. The incisions were sutured layer by layer with a 5-0 absorbable suture, and the penis was appropriately subjected to pressure bandaging.

After surgery, the penis was bandaged with an elastic bandage, the drug was changed daily and the wound condition and blood supply of the skin was observed.

The penis had a circumferential diameter of 7.8 cm in natural state before surgery, and a circumferential diameter of 12 cm in natural state after surgery.

The wound was healed 14 days after surgery, and the sexual function was measured to be normal. A following visit was made 6 to 8 months after surgery. The time of sexual life was prolonged to 20 to 30 min. The degree of satisfaction with sexual life was high, and the harmonious degree of sexual life was improved.

Although the present invention has been described in detail as above with the aid of the general description and specific embodiments, it will be apparent to those skilled in the art that modifications or improvements can be made thereto based on the present invention. Therefore, such modifications or improvements made without departing from the spirit of the present invention are intended to be within the scope of protection of the present invention.

INDUSTRIAL APPLICABILITY

The present invention provides a built-in bio-sleeve and preparation method thereof. The new acellular allogeneic dermal matrix material prepared by the present invention is manufactured into a built-in bio-sleeve, which can be used for the treatment of premature ejaculation and short and small penis, and provides a suitable built-in bio-sleeve material for the dorsal nerve isolation surgery and the penis enlargement surgery. The acellular allogeneic dermal matrix or the built-in bio-sleeve of the present invention is used for the dorsal nerve isolation surgery, the penis enlargement or lengthening surgery without cutting off the dorsal nerve, thereby avoiding the probability of psychological erectile dysfunction caused by the patient's worry about cutting off the dorsal nerve. The acellular allogeneic dermal matrix or the built-in bio-sleeve of the present invention has high economic value and good application prospects.

What is claimed is:

1. A preparation method of an acellular allogeneic dermal matrix, characterized in that, the method comprises the following steps:
    Step 1), an allogeneic skin material is put into a solution of an enzyme(s), soaked and subjected to shaking treatment to obtain a semi-finished product A, wherein the enzyme is phospholipase, or the enzymes are phospholipase and protease;
    Step 2), the semi-finished product A is taken out, soaked with physiological saline, and subjected to shaking treatment to obtain a semi-finished product B;
    Step 3), the semi-finished product B is put into a surfactant solution, and subjected to ultrasonic soaking treatment to obtain a semi-finished product C;
    Step 4), the semi-finished product C is soaked with physiological saline, and subjected to shaking treatment to obtain a semi-finished product D;
    Step 5), the semi-finished product D is put into a container containing a DNA hydrolase solution, and subjected to shaking treatment to obtain a semi-finished product E;
    Step 6), the semi-finished product E is soaked with physiological saline, and subjected to shaking treatment to obtain a semi-finished product F; and
    Step 7): the semi-finished product F is washed and soaked with water for injection to obtain a finished product G.

2. The preparation method according to claim 1, characterized in that, the phospholipase in the step 1) is one or more of phospholipase A1, phospholipase A2, phospholipase C, and phospholipase D; and more preferably, the phospholipase is a mixture of phospholipase A1, phospholipase A2, phospholipase C, and phospholipase D at a mass ratio of 1:1:1:1; and/or,
    the protease includes one or more of trypsin, bromelain, papain, and dispase.

3. The preparation method according to claim 1, characterized in that, the solution of an enzyme(s) in the step 1) has a pH of 7.0 to 8.0;
    the concentration of the phospholipase is 0.1 g/L to 0.4 g/L; and
    the concentration of the protease is 0.1 g/L to 0.3 g/L.

4. The preparation method according to claim 1, characterized in that, the conditions for shaking treatment in the step 1) are as follows: shaking for 0.5 h to 4 h at a shaking speed of 10 rpm to 200 rpm and a temperature of 10° C. to 40° C.

5. The preparation method according to claim 1, characterized in that, the surfactant solution in the step 3) contains 0.1 to 0.3 g/L of SDS, or the surfactant solution contains 0.1 to 0.3 g/L of Triton X-100;
    the conditions for ultrasonic soaking are as follows: ultrasonic treatment for 3 to 8 min under 40 to 80 KHz and 100 to 400 W, soaking for 2 to 4 h, and repeating the above operation for 2 to 4 times, at a temperature of 1 to 20° C.

6. The preparation method according to claim 1, characterized in that, the DNA hydrolase solution in the step 5) has a concentration of 4 to 8 g/L and a pH of 7.0 to 8.0; and/or,
    the conditions for shaking treatment in the step 5) are as follows: shaking for 2 to 8 h at a shaking speed of 10 to 200 rpm and a temperature of 10 to 40° C.

7. The preparation method according to claim 1, characterized in that, the conditions for shaking treatment in the step 2), the step 4) and the step 6) are as follows: shaking is conducted for 1 to 2 h at a shaking speed of 80 to 150 rpm, then the physiological saline is replaced to continue the shaking treatment, and the operation is repeated for 4 to 6 times, at a temperature of 1 to 5° C.; and/or,
    the conditions for washing and soaking with water for injection in the step 7) are as follows: shaking is conducted for 2 h at a shaking speed of 80 to 150 rpm and a temperature of 1 to 5° C., then the water for injection is replaced to continue the shaking treatment, and the operation is repeated for 4 to 6 times.

8. The method according to claim 1, further comprising:
    Step 9): the finished product G is taken out, placed in a solution containing a lyoprotectant for freeze-drying, packaged, and sterilized to obtain a finished product H.

9. The preparation method according to claim 8, characterized in that, the freeze-drying in the step 9) comprises: placing the finished product G into an drying oven at 5° C., holding for 1 h, cooling to −40° C. and holding for 1 h, heating to −18° C. and holding for 1 h, cooling again to −35° C. and holding for 1 h, starting a vacuum pump to evacuate the drying oven to a vacuum degree of 5 to 10 Pa; heating a partition board to −30° C. in 2 h, evacuating the drying oven to a vacuum degree of 1 to 5 Pa and holding for 15 h; heating the partition board to 0° C. in 1 h and holding for 10 h, then measuring the pressure rise until the pressure rise is less than 1 Pa; heating the partition board to 10° C. in 1 h and holding for 10 h, and measuring the pressure rise until the pressure rise is less than 1 Pa; heating the partition board to 25° C. in 0.5 h and holding for 8 h, and measuring the pressure rise until the pressure rise is less than 1 Pa; and the vacuum degree in said oven is not higher than 30 Pa throughout the drying process.

10. The method according to claim 1, further comprising:
   Step 8): the finished product G is taken out, packaged, and sterilized to obtain a finished product H.

11. The preparation method according to claim 8, characterized in that, the lyoprotectant solution in the step 9) is composed of a phosphate buffer solution, hyaluronic acid and sugar, wherein the concentration of the hyaluronic acid is 0.4 to 0.8 mg/100 mL, the concentration of the sugar is 10 to 20 mg/100 mL, and the sugar is one or more of trehalose, lactose, sucrose, glycerin, mannitol, sorbitol, mannose, and glucose; optionally wherein the phosphate buffer solution has a concentration of 10 mmol/L and a pH of 7.0.

\* \* \* \* \*